(12) United States Patent
Kim et al.

(10) Patent No.: US 7,998,078 B2
(45) Date of Patent: *Aug. 16, 2011

(54) ULTRASONIC PROBE HAVING A DEVICE FOR COUPLING A WIRE-ROPE TO A TRANSDUCER

(75) Inventors: Seong Rae Kim, Seoul (KR); Won Soon Hwang, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 722 days.

This patent is subject to a terminal disclaimer.

(21) Appl. No.: 11/968,901

(22) Filed: Jan. 3, 2008

(65) Prior Publication Data

US 2008/0161695 A1 Jul. 3, 2008

(30) Foreign Application Priority Data

Jan. 3, 2007 (KR) .................. 10-2007-0000615

(51) Int. Cl.
*A61B 8/14* (2006.01)
(52) U.S. Cl. .................. 600/459; 600/407; 600/437
(58) Field of Classification Search .................. 600/407, 600/437; 601/2
See application file for complete search history.

(56) References Cited

U.S. PATENT DOCUMENTS

| | | | | | |
|---|---|---|---|---|---|
| 4,203,324 | A | * | 5/1980 | Baumoel | 73/290 V |
| 5,351,692 | A | * | 10/1994 | Dow et al. | 600/463 |
| 5,833,616 | A | | 11/1998 | Gruner et al. | |
| 2006/0017330 | A1 | | 1/2006 | Botos et al. | |
| 2008/0161694 | A1 | | 7/2008 | Kim | |

FOREIGN PATENT DOCUMENTS

| | | |
|---|---|---|
| EP | 1 744 178 A2 | 1/2007 |
| KR | JP 10-2008-0060728 | 7/2008 |

* cited by examiner

*Primary Examiner* — Tse Chen
*Assistant Examiner* — Joel F Brutus
(74) *Attorney, Agent, or Firm* — Oblon, Spivak, McClelland, Maier & Neustadt, L.L.P.

(57) ABSTRACT

Embodiments of the present invention may provide an ultrasonic probe having a device for coupling a wire-rope to a transducer. A worker can easily couple the wire-rope to the transducer and can conveniently adjust the tension of the wire-rope. The ultrasonic probe has a pair of wire-ropes transmitting a drive force from a driving portion to the transducer by alternately pulling it at both sides thereof for rotating the transducer. The device comprises a wire-rope tightening bolt having a through-hole to which a wire-rope is inserted, wherein the wire-rope tightening bolt is rotatably coupled to the transducer.

4 Claims, 5 Drawing Sheets

ULTRASONIC PROBE HAVING A DEVICE FOR COUPLING A WIRE-ROPE TO A TRANSDUCER The present application claims priority from Korean Patent Application No. 10-2007-0000615 filed on Jan. 3, 2007, the entire subject matter of which is incorporated herein by reference.

BACKGROUND

1. Field

The present invention generally relates to an ultrasonic probe, and more particularly, to an ultrasonic probe having a device for coupling a wire-rope to a transducer for use with an ultrasonic diagnostic apparatus.

2. Background

An ultrasonic diagnostic apparatus is widely used to diagnose a subject by visualizing a portion of the subject's body. For example, the ultrasonic diagnostic apparatus diagnoses a subject by detecting alien substances of organs, measuring the level of a lesion, or observing a tumor or a fetus. Such ultrasonic diagnostic apparatus generally employs various ultrasonic probes in order to obtain information on a subject's body. The ultrasonic probe has a transducer, which emits ultrasonic waves into an inspection portion of a subject and receives the reflected ultrasonic waves therefrom to convert the reflected ultrasonic waves into electric signals. The ultrasonic diagnostic apparatus processes the electric signals from the ultrasonic probe, thereby forming an ultrasonic mage that shows the inspection portion of a subject's body. In the recent years, ultrasonic probes configured to rotate the transducer are used to obtain a more accurate or three-dimensional ultrasonic image. Such ultrasonic probes employ a device for rotating a transducer therein. The device for rotating a transducer may be configured to transmit a drive force from a drive motor to the transducer via a pair of wire-ropes, which can absorb a shock produced during a rotation of the transducer.

One example of a prior art ultrasonic probe for conducting a three-dimensional imaging is shown in FIGS. 1 to 3.

As shown in FIGS. 1 and 2, the prior art ultrasonic probe includes a cover 10, which may be in contact with a subject to be inspected and a case 20 for accommodating a transducer with a plurality of ultrasonic elements. The transducer may be rotated in the cover 10 so that three-dimensional ultrasonic imaging can be made.

A device for rotating the transducer is mounted inside the case 20. The device comprises: a step motor 110; a speed reducer having a drive pulley (not shown), a driven pulley 130 and a belt 120 connecting the drive pulley and the driven pulley 130; a wire-rope holder 150 coupled to the speed reducer by a shaft 140; a transducer 170 having a plurality of ultrasonic elements and a rotating shaft 175; and a pair of wire ropes 160, one ends of which are connected to the wire-rope holder 150 and the other ends of which are connected to both lateral sides of the transducer 170. The wire-rope holder 150 includes a buffer spring 151 for absorbing a shock on the wire-ropes 160 during rotation of the transducer 170.

The transducer 170 includes: a plurality of the ultrasonic elements 171; a transducer holder 172 for coupling the transducer to the rotating shaft 175; and a pair of wire-rope guides 173 having a slit 174 for coupling the other end of each wire-rope 160 thereto. Thus, one end of each wire-rope 160 is knotted to the wire-rope holder 150, while the other end thereof is coupled to the slit 174 of the wire-rope guide 173.

As shown in FIGS. 2 and 3, the wire-rope holder 150 has a buffer spring 151, both ends of which are bent like a hook. One end of each wire-rope 160 is knotted to each end of the buffer spring 151. A coupler 162 is provided at the other end of each wire-rope 160. The one end of the wire-rope 160 is inserted in the slit 174 as the coupler 162 is caught in the slit 174.

In the above-described ultrasonic probe, one end of each wire-rope 160 is first caught by each end of the buffer spring 151, while the other end thereof is then hooked to the slit 174 of the transducer 170. Accordingly, there is a problem with the wire-rope coupling of the prior art ultrasonic probe in that the worker must apply a large force to each wire rope 160. This is so that the buffer spring 151 expands sufficiently enough in order to hook the other end of the wire-rope to the slit 174.

There is a further problem with the prior art ultrasonic probe in that a tension applied to the wire-rope cannot be adjusted since the length of the wire-rope cannot be changed once the ultrasonic prove is assembled.

BRIEF DESCRIPTION OF THE DRAWINGS

Arrangements and embodiments may be described in detail with reference to the following drawings in which like reference numerals refer to like elements and wherein.

DETAILED DESCRIPTION OF THE PRESENT INVENTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

An ultrasonic probe having a device for coupling a wire-rope to a transducer, which is constructed in accordance with an embodiment of the present invention, will be now described in detail with reference to FIGS. 4 to 6.

Figure 1:
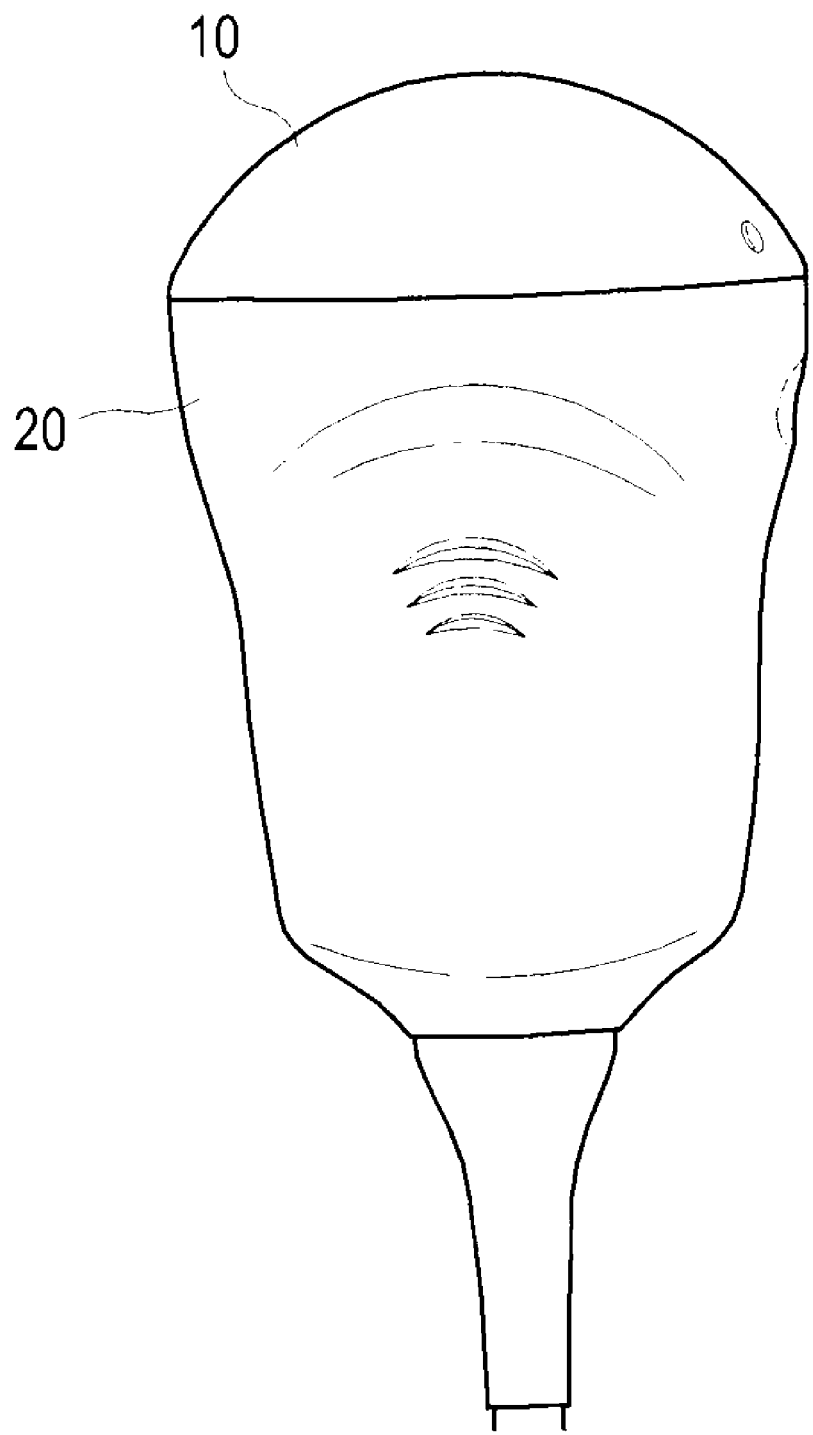
FIG. 1 is a front view of a prior art ultrasonic probe for conducting a three-dimensional imaging.
Figure 2:
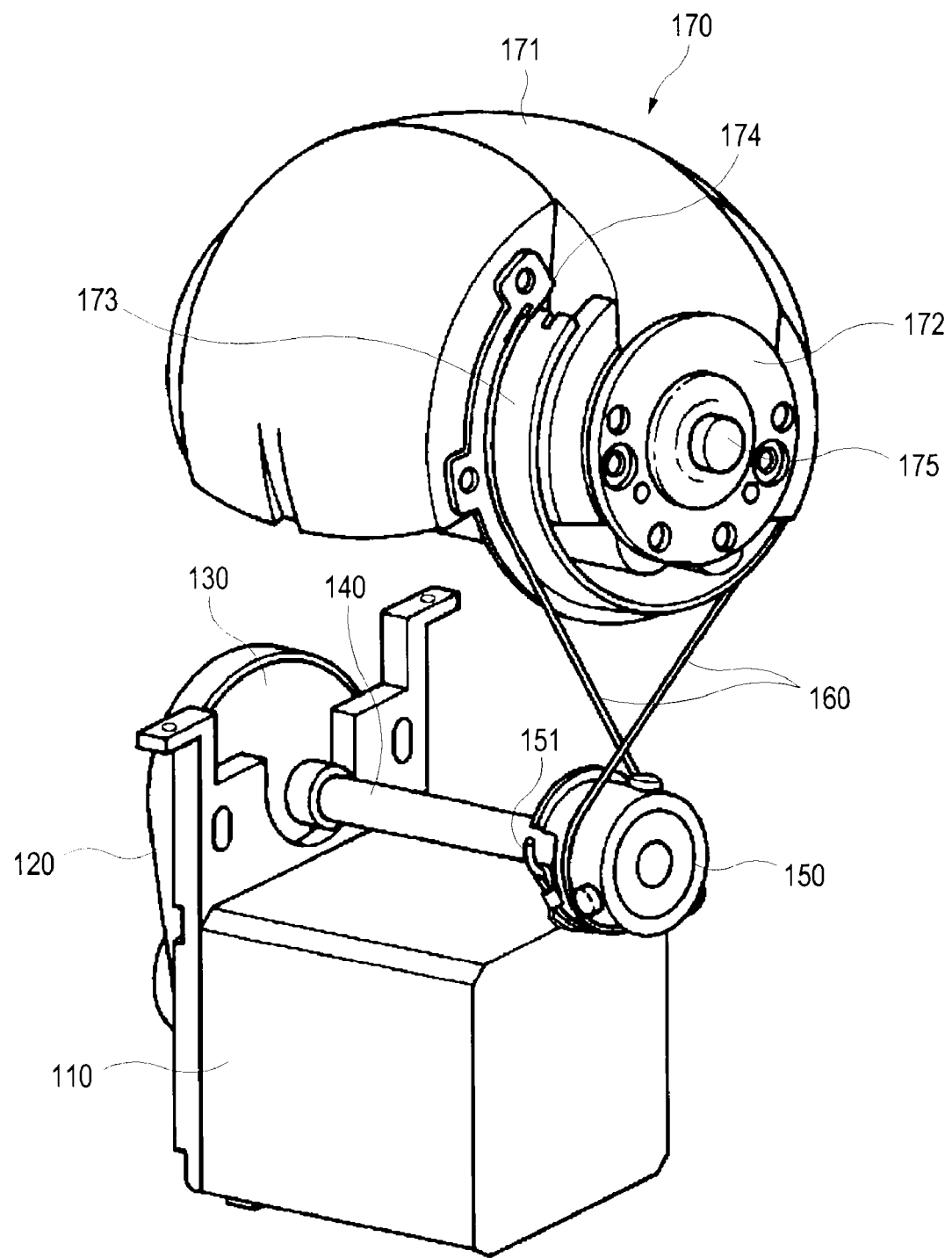
FIG. 2 is a perspective view showing an internal structure of the prior art ultrasonic probe for conducting the three dimensional imaging.
Figure 3:
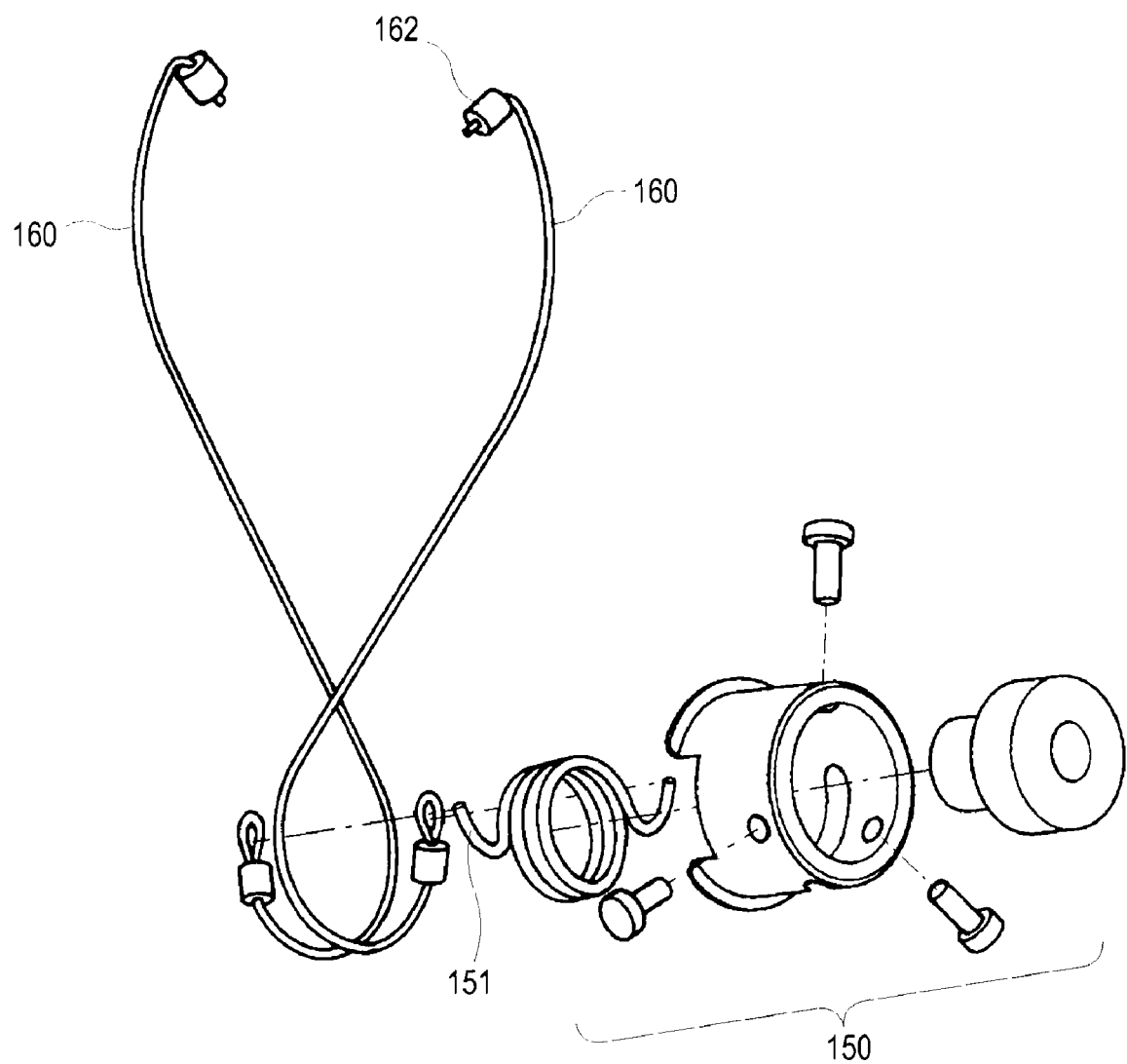
FIG. 3 is an exploded view showing a wire-rope holder of the prior art ultrasonic probe shown in FIG. 2.
Figure 4:
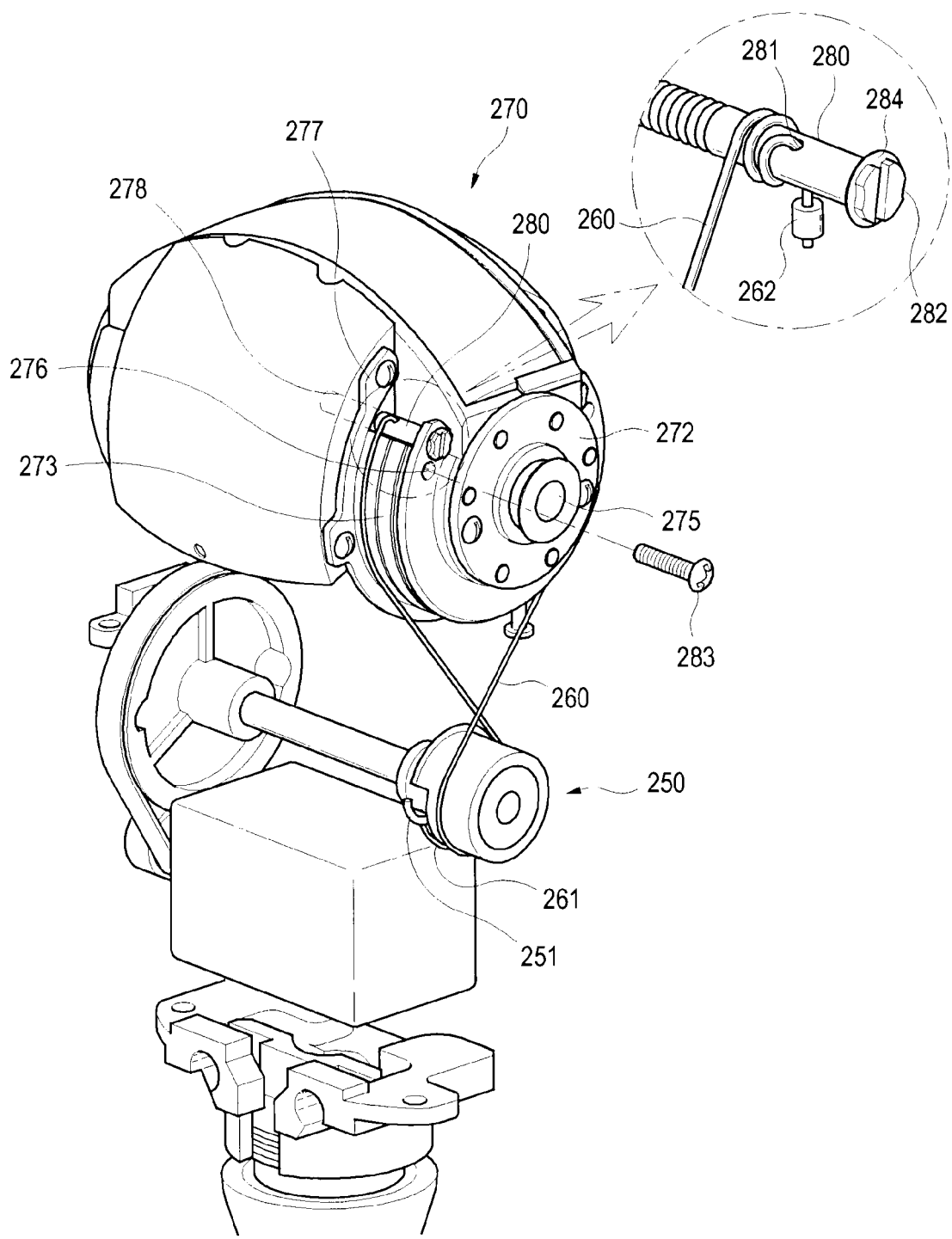
FIG. 4 is a perspective view showing an internal structure of an ultrasonic probe for three-dimensional imaging with a device for coupling a wire-rope to a transducer constructed in accordance with an embodiment of the present invention.
Figure 5:
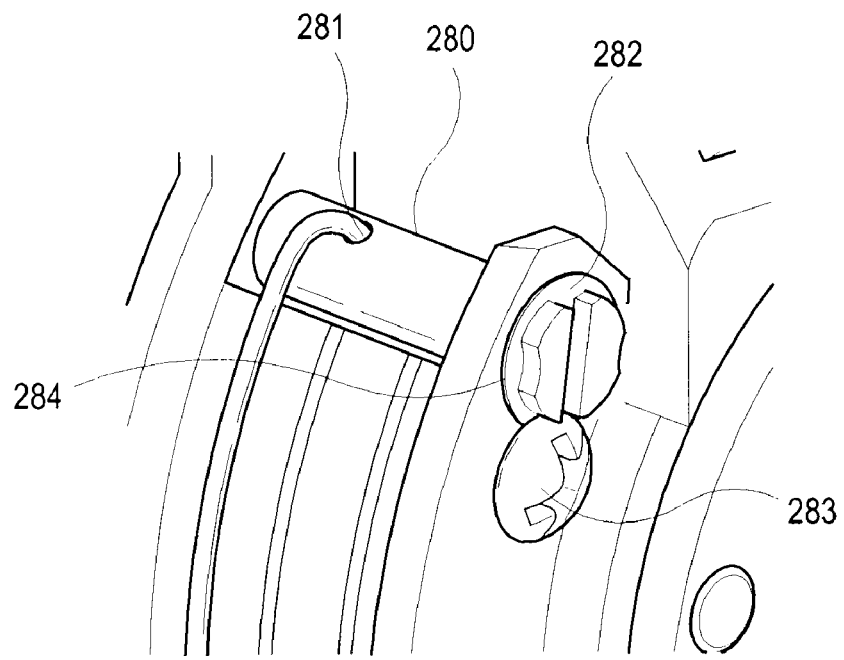
FIG. 5 is an enlarged perspective view of the device for coupling a wire-rope to a transducer of the ultrasonic probe shown in FIG. 4.
Figure 6:
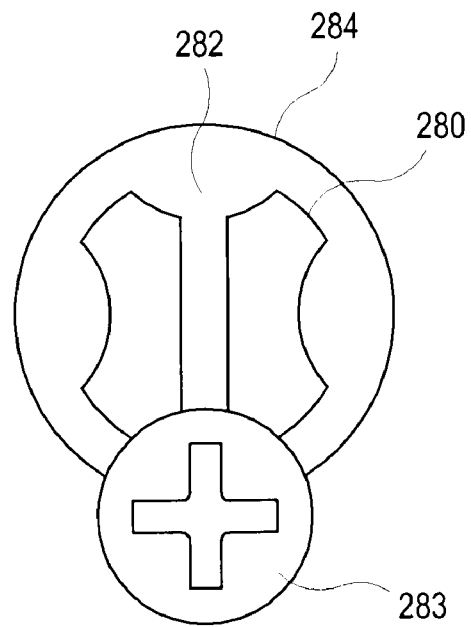
FIG. 6 is a side view of the device for coupling a wire-rope to a transducer shown in FIG. 5.

As shown in FIGS. 4 to 6, one end of each wire rope 260 is hooked to a wire-rope holder 250. More specifically, a knot 261 provided at one end of the wire-rope 260 is hooked to a buffer spring 251 of the wire-rope holder 250. The buffer spring 251 is a coil spring with both ends bent like a hook for coupling the knot 261 of the wire-rope 260 thereto. A pair of wire ropes 260 are disposed in the shape of 8-figure.

The other end of each wire-rope 260 is coupled to a transducer 270. Each wire-rope 260 is guided by a wire-rope guide 273. A coupler 262 is provided at the other end of the wire-rope 260. A wire-rope tightening bolt 280 is fastened to the transducer 270. A through-hole 281 is formed at the wire-rope tightening bolt 280. The wire-rope 260 is inserted through the through-hole 281. The coupler 262 prevents the wire-rope 260 from unfastening from the wire-rope tightening bolt 280.

The transducer 270 further includes: a bracket 277 for fixing the wire-rope guide 273 to the transducer 270; and a first threaded hole 278 formed at a lateral side thereof. At least one holding groove 282 is formed at a periphery of a head of the wire-rope tightening bolt 280. Preferably, the shape of the groove 282 corresponds to the head shape of a screw 283. Further, a washer 284 is formed around the head of the wire-rope tightening bolt 280. The wire-rope tightening bolt 280 is inserted into the first threaded hole 278.

A second threaded hole 276 is formed at the lateral side of the transducer 270 so as to be parallel to the first threaded hole 278. A screw 283 is fastened in the second threaded hole 276. To completely fasten the screw 283, the head of the screw 283 is engaged to one of the holding grooves 282 to thereby hold the wire-rope tightening bolt 280 in position. Thus, the wire-rope tightening bolt 280 is prevented from being rotated as its head and the head of the screw 283 are engaged to each other. Accordingly, the wire-rope 260 can maintain its tension. Further, since the screw 283 presses the washer 284 of the wire-rope tightening bolt 280, the coupling between the wire-rope tightening bolt 280 and the transducer 270 can be intensified.

The coupling process of the wire-rope will now be described with reference to FIGS. 4 to 6.

One end of each wire-rope 260 is hooked to the bent end of the buffer spring 251 of the wire-rope holder 250. The wire ropes 260 are disposed as being crossed to each other, while the other ends thereof are coupled to the transducer 270. Each wire-rope 260 is first inserted into the through-hole 281. Then, the coupler 262 is attached to the other end of the wire-rope 260. Thereafter, the wire-rope tightening bolt 280 is screw-engaged to the first threaded hole 278. As the wire-rope tightening bolt 280 is rotated, the wire rope 260 is tightened or slackened off accordingly.

If a desired tension is applied to the wire-rope 260, then the screw 283 is screw-engaged to the second threaded hole 276 of the transducer 270. In such a case, the head of the screw 283 is engaged to one of the holding grooves 282 of the wire-rope tightening bolt 280. Thus, the wire-rope tightening bolt 280 cannot be rotated at all and the desirably applied tension of the wire-rope 260 can be maintained as it is.

Accordingly, a worker assembling the ultrasonic probe does not need to apply any force to the buffer spring 251 to connect the wire-rope 260 to the transducer 270. In addition, the worker can easily tighten or slacken the wire-rope 260 only by using a small driver.

Further, the tension of the wire-rope can be precisely or desirably adjusted only by varying the fastening extent of the wire-rope tightening bolt 280. Thus, the transducer 270 can be rotated precisely without any error due to the wire-rope 260 with a constant tension applied thereto. Moreover, the ultrasonic probe comprising such wire-rope coupling device allows a more accurate three-dimensional imaging.

Embodiments of the present invention may provide an ultrasonic probe comprising a pair of alternately pulled wire-ropes for transmitting a drive force from a drive portion to a transducer and a device for coupling the wire-rope to the transducer. The device may comprise a bolt rotatably coupled to the transducer for tightening the wire-rope. The bolt may have a through-hole, into which the wire-rope is inserted and to which the wire-rope is coupled.

The device may further comprise a wire-rope coupler provided at one end of the wire-rope inserted into the through-hole. The wire-rope coupler may prevent the wire rope from unfastening from the through-hole. The other end of the wire-rope may be hooked to the drive portion.

The bolt may be screw-engaged to the transducer.

The bolt may include a head having at least one holding groove at a periphery thereof. A device may further include a screw coupled to the transducer. The screw may have a head engaged to one of the holding grooves. The bolt may further include a washer pressed by the head of the screw.

Any reference in this specification to "one embodiment," "an embodiment," "example embodiment," etc., means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments of the present invention.

Although embodiments of the present invention have been described with reference to a number of illustrative embodiments thereof, it should be understood that various other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasonic probe comprising:
   a transducer;
   a pair of wire-ropes, each of the wire-ropes being coupled to the transducer via a wire-rope tightening bolt having a through-hole so as to receive the respective wire-ropes, the wire-rope tightening bolt being rotatably coupled and screw-engaged to the transducer for tightening the respective wire-ropes, the wire-rope tightening bolt including a head having at least one holding groove at a periphery thereof;
   a drive unit configured to drive the pair of wire-ropes, wherein said wire-ropes are alternately pulled by the drive unit to rotate the transducer; and
   a screw coupled to the transducer, the screw having a head engaging to the holding groove of the head of the wire-rope tightening bolt.

2. The ultrasonic probe of claim 1, further comprising a wire-rope coupler provided at one end of each of the wire-ropes inserted into the through-hole, and wherein the wire-rope coupler prevents each of the wire-ropes from unfastening from the through-hole.

3. The ultrasonic probe of claim 2, wherein the other end of each of the wire-ropes is hooked to the drive unit.

4. The ultrasonic probe of claim 1, wherein the wire-rope tightening bolt further includes a washer pressed by the head of the screw.

* * * * *